US00PP18109P3

(12) United States Plant Patent
Stemkens

(10) Patent No.: US PP18,109 P3
(45) Date of Patent: Oct. 2, 2007

(54) ***SUTERA* PLANT NAMED 'SUTCACOMWI'**

(50) Latin Name: *Sutera diffusa*
Varietal Denomination: Sutcacomwi

(75) Inventor: Henricus G. W. Stemkens, Hoorn (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 11/301,474

(22) Filed: Dec. 13, 2005

(65) Prior Publication Data

US 2007/0136911 P1 Jun. 14, 2007

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
*Assistant Examiner*—S. B. McCormick-Ewoldt
(74) *Attorney, Agent, or Firm*—Bruce Vrana

(57) ABSTRACT

A new and distinct variety of *Sutera* plant, substantially as herein illustrated and described, characterized particularly as to novelty by larger white flowers than other *Sutera* plants, earlier to flower, by thick stems and a growing habit that is compact.

1 Drawing Sheet

Latin name of the genus and species of the plant claimed: *Sutera diffusa.*
Varietal denomination: 'Sutcacomwi'.

BACKGROUND OF THE NEW PLANT

The present invention comprises a new distinct cultivar of *Sutera,* botanically known as *Sutera diffusa.*

The new cultivar is propagated from cuttings resulting from the cross of 'B0078-1' and 'B0079-1'. 'B0078-1' is a white flowering *Sutera.* 'B0078-1' is not commercially available and is not known by any synonyms. 'B0079-1' is a white flowering *Sutera.* 'B0079-1' is not commercially available and is not known by any synonyms. Neither 'B0078-1' nor 'B0079-1' has been patented.

As a result of this cross the present cultivar was created in 2001 in Enkhuizen, Netherlands and has been repeatedly asexually reproduced by cuttings in Enkhuizen, Netherlands and Sarrians, France over a three year period. It has been found to retain its distinctive characteristics through successive propagations. The new variety is stable and reproduces true to type in successive generations of asexual reproduction.

The new *Sutera* plant is an annual in most climatical zones in the US, only in zones 9 and 10 it is a perennial plant.

SUMMARY OF THE INVENTION

It was found that the cultivar of the present invention:

a) exhibits white flowers;

b) has thick stems; and c) exhibits a compact growth habit.

DESCRIPTION OF THE DRAWING

This new *Sutera* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Sutera.* The data which defines these characteristics were collected from asexual reproductions carried out in Enkhuizen, Netherlands. The plant history was taken on 15 weeks old plants, cultured in 10.5 cm containers, blossomed under natural light in a greenhouse.

Color readings were taken in the greenhouse under ambient light. Color references are primarily to The R.H.S. Colour Chart of The Royal Horticultural Society of London.

TABLE 1

Differences between the new cultivar 'Sutcacomwi', its parents and a similar cultivar

| | 'Sutcacomwi' | 'B0078-1' | 'B0079-1' | 'Sutcatrwhi' (U.S. Plant Patent No. 17,237) |
|---|---|---|---|---|
| Flower color | White | White | White | White |
| Stem thickness | 3-4 mm | 2 mm | 3-4 mm | 3-4 mm |
| Plant habit | Compact | Trailing | Compact | Trailing |
| Flower size | Big | Big | Small | Medium |

The plant:

*Classification.*—Botanical: *Sutera diffusa.*

*Parentage.*—Female parent: A seedling named 'B0078-1' is one of our seedlings from our B-generation of plants bred in 1999. Pollen parent: A seedling named 'B0079-1' is one of our seedlings from our B-generation of plants bred in 1999.

*Growth habit.*—Compact.

*Plant height.*—15–18 cm.

*Speading area of plant.*—20–25 cm.

*Growth rate.*—Rapid growing.
*Strength.*—Good.
*Branching habit.*—Short internodes and on each knot more than two appearing shoots give a plant that is more branched than normal.
*Blooming period.*—From May until November.

The stem:
*Diameter.*—2–4 mm.
*Shape.*—Cylindrical.
*Anthocyan pigmentation.*—Absent.
*Color of the stem.*—137A.
*Length of internode.*—8–14 mm.
*Pubescence.*—Sparse.

The foliage:
*Phyllotaxis.*—Opposite.
*Shape of blade.*—Broadly ovate.
*Shape of blade apex.*—Rounded.
*Shape of blade base.*—Shortly attenuate.
*Leaf margin.*—Crenate.
*Venation.*—Pinnate.
*Texture.*—Upper side: Smooth, glabrous. Lower side: Slightly pubescent.
*Length.*—14–25 mm.
*Width.*—16–24 mm.
*Thickness.*—1–2 mm.
*Depth of incision.*—1 mm.
*Color.*—Upper side: 137A. Lower side: 137B.
*Length of petiole.*—1 mm.
*Diameter of petiole.*—1 mm.
*Color of petiole.*—137B.
*Fragrance.*—Musk.

The bud:
*Pedicel length.*—8–14 mm.
*Pedicel diameter.*—1 mm.
*Pedicel color.*—137C.
*Pedicel angle.*—About 60 degrees from the stem.
*Bud size.*—Diameter: 1 mm. Length: 4–8 mm.
*Bud shape.*—Obovate.
*Bud color.*—85C.
*Sepals.*—Color: 137C. Shape: Erect calyx. Number: 5. Size: 1 mm.

The flower:
*Flower diameter.*—12–17 mm.
*Tube length.*—4–8 mm.
*Throat diameter, distal end.*—2–3 mm.
*Tube diameter, proximal end.*—1.5–2.5 mm.
*Form.*—Salverform.
*Symmetry.*—Radial symmetric.
*Type.*—Solitary, axillary.
*Color.*—Upper surface: N155C. Lower surface: N155C.
*Corolla tube.*—Cylindrical.
*Corolla tube color.*—8C.
*Overlapping of petals.*—Separate.
*No. of petals.*—5.
*Shape of petals.*—Gamopetalous, grown together at the base of the petal, forming a corolla.
*Petal lobe.*—Length: 4–7 mm. Width: 3–4 mm. Shape: Spatulate. Apex: Rounded. Margin: Entire. Texture: Smooth.
*Shape of sepals.*—Gamopetalous, grown together at the base of the petal.
*Calyx.*—Length: 6–8 mm. Diameter: 3 mm. Shape: Narrow, linear. Apex: Acute. Margin: Entire.
*Texture of the calyx.*—Upper surface: Pubescent. Lower surface: Pubescent.
*Color of the calyx.*—Upper surface: 137c. Lower surface: 137C.
*Anthocyan pigmentation of calyx limb.*—Absent.
*Flower fragrance.*—No fragrance detected.
*Lastingness of a single flower.*—Flowers stay open 8–11 days.

The reproductive organs:
*Number of reproductive organs.*—1 pistil, 4 stamens.
*Pollen production.*—Very low.
*Stigma color.*—Light green 138D.
*Stamen color.*—Yellow 13A.
*Stamen arrangement.*—Didynamous.
*Stamen type.*—Basifixed.
*Dehiscence of stamens.*—Extrorse.
*Ovary position.*—Ovary superior, flower hypogynous.
*Style shape.*—Style terete.
*Style length.*—5 mm.
*Pistil length.*—8 mm.

Seeds: Only few seeds are formed, almost sterile plant.

The roots:
*Type of roots.*—Fibrous, color 155A.

Physiological and ecological characteristics: No exceptional physiological and ecological differences with other cultivars of *Sutera diffusa* are observed.

Propagation: Propagation is done by axillary cuttings. Tips of stems are used, which take 6 days to initiate roots and 12 days to develop roots.

What is claimed is:

1. A new and distinct cultivar of *Sutera* plant named 'Sutcacomwi,' as substantially illustrated and described herein.

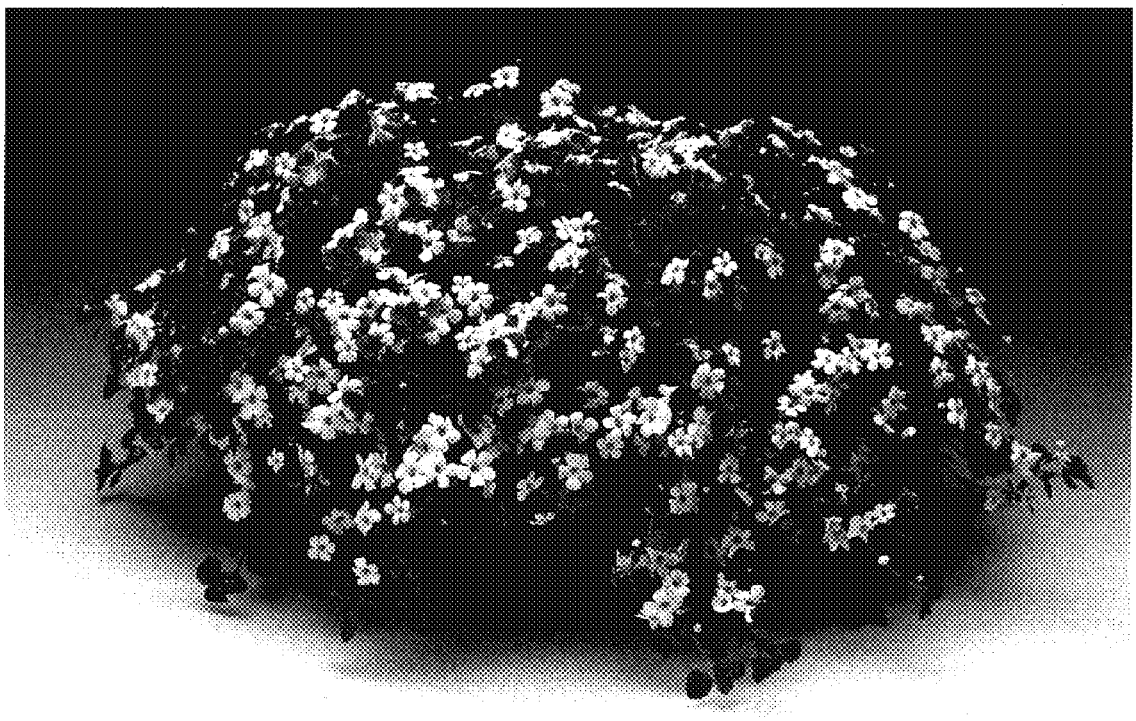

* * * * *